United States Patent [19]

Shiber

[11] Patent Number: 5,041,082
[45] Date of Patent: Aug. 20, 1991

[54] MECHANICAL ATHERECTOMY SYSTEM AND METHOD

[76] Inventor: Samuel Shiber, P.O. Box 371, Mundelein, Ill. 60060

[21] Appl. No.: 18,083

[22] Filed: Feb. 24, 1987

Related U.S. Application Data

[63] Continuation-in-part of Ser. No. 874,546, Jun. 16, 1986, Pat. No. 4,732,154, which is a continuation-in-part of Ser. No. 609,846, May 14, 1984, abandoned.

[51] Int. Cl.⁵ .............................................. A61B 17/32
[52] U.S. Cl. ...................................... 604/22; 606/159
[58] Field of Search ..................... 128/305, 305.1, 310, 128/751, 753, 754; 604/22; 606/159, 180

[56] References Cited

U.S. PATENT DOCUMENTS

| | | | |
|---|---|---|---|
| 1,123,730 | 1/1915 | Greenfield | 128/310 |
| 1,596,754 | 8/1926 | Moschelle | 604/282 |
| 2,505,358 | 4/1950 | Gusberg et al. | 128/751 |
| 3,614,953 | 10/1971 | Moss | 128/305.1 |
| 4,030,503 | 6/1977 | Clark | 128/356 X |
| 4,177,797 | 12/1979 | Baylis et al. | 128/754 |
| 4,249,541 | 2/1981 | Pratt | 128/753 |
| 4,306,570 | 12/1981 | Matthews | 128/310 X |
| 4,445,509 | 5/1984 | Auth | 128/305 |
| 4,479,497 | 10/1984 | Fogarty et al. | 128/344 |
| 4,589,412 | 5/1986 | Kensey | 128/305 |
| 4,627,436 | 12/1986 | Leckrone | 128/303.1 |
| 4,672,962 | 6/1987 | Hershenson | 128/303.1 |

FOREIGN PATENT DOCUMENTS

| | | | |
|---|---|---|---|
| 163502 | 12/1985 | European Pat. Off. | 128/328 |
| 2804015 | 8/1979 | Fed. Rep. of Germany | 128/305 |
| 665908 | 6/1979 | U.S.S.R. | 128/304 |
| 2044103 | 10/1980 | United Kingdom | 128/754 |

Primary Examiner—Michael H. Thaler

[57] ABSTRACT

A mechanical atherectomy system insertable into a patient's artery over a non-rotating, auger-shaped flexible guide-wire for remotely cutting and removing an obstruction therein, having a flexible rotary-catheter equipped with a tubular-blade at its front end and a motor connected to its other end.

27 Claims, 2 Drawing Sheets

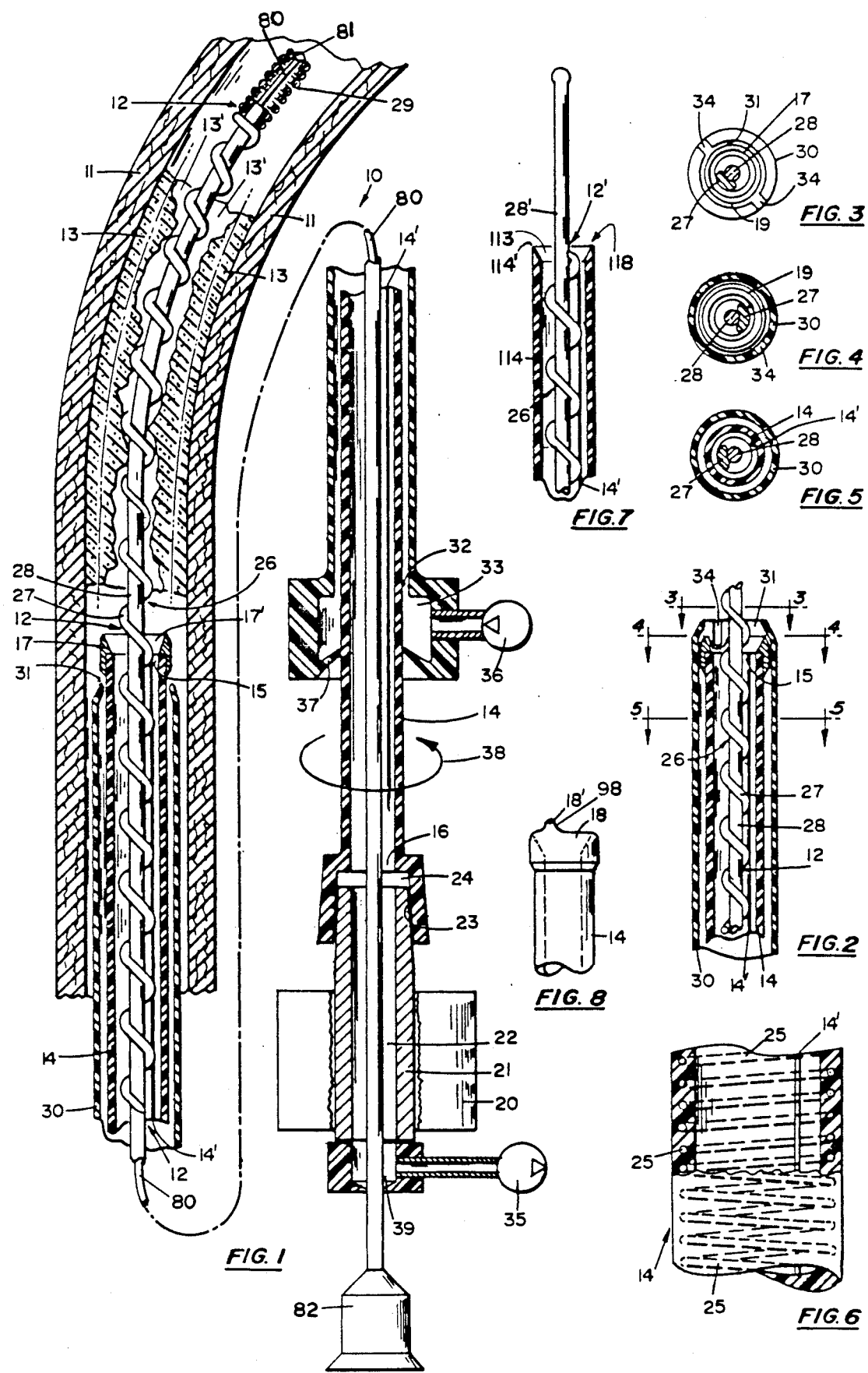

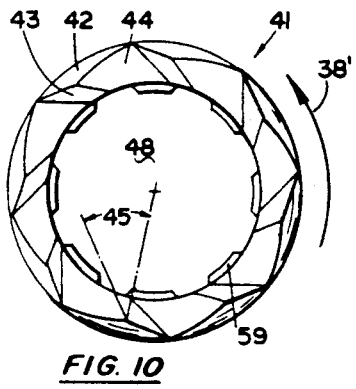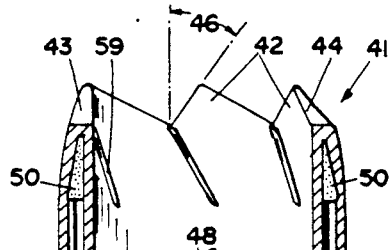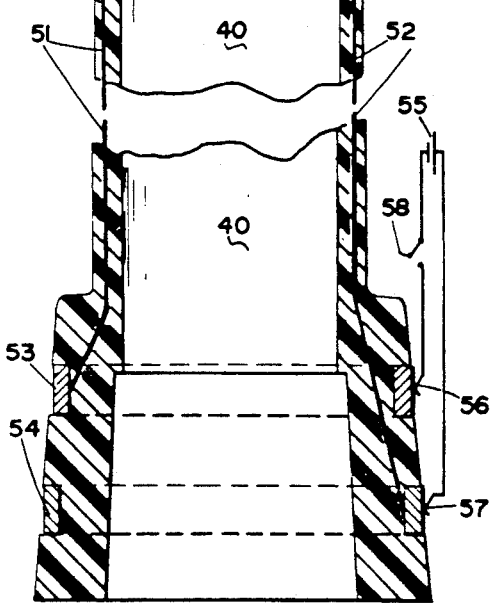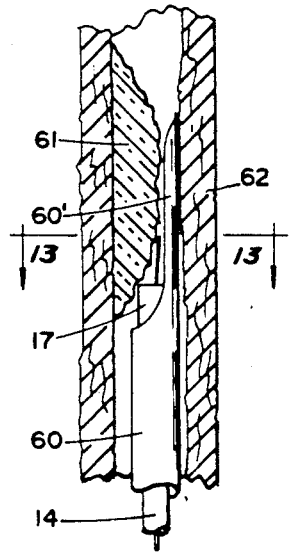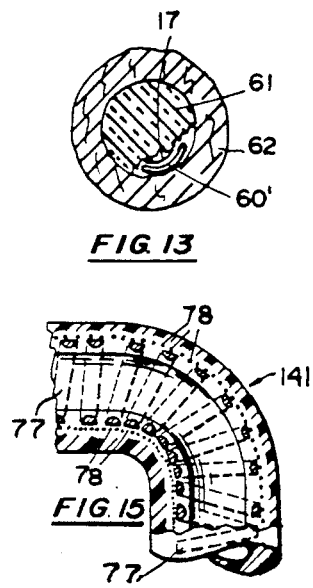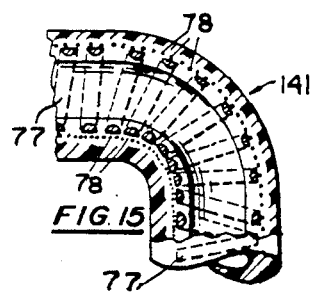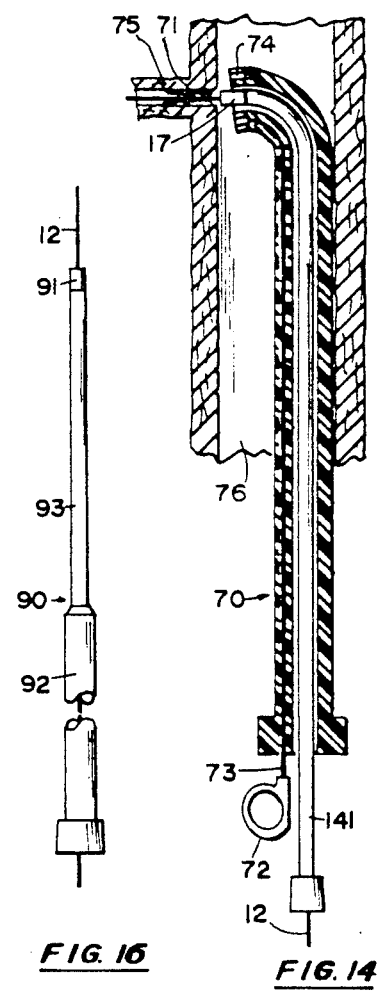

MECHANICAL ATHERECTOMY SYSTEM AND METHOD

CROSS REFERENCE TO OTHER APPLICATIONS

This application is a continuation in part of application Ser. No. 06/874,546 now U.S. Pat. No. 4,732,154 which was filed on June 16, 1986 and which is a continuation in part of application Ser. No. 06/609,846 which was filed on May 14, 1984 now abandoned. Both prior applications are hereby being incorporated by reference.

BACKGROUND AND OBJECTIVES OF THE INVENTION

With age a large portion of the population develops arterial obstructions formed by fats, fibrous material and calcified deposits, resulting in a diminished blood circulation. The disturbance to blood flow that these obstructions cause can induce blood clots which further diminish or block the blood flow. When this process occurs in the arteries serving the heart muscles it is referred to as a heart attack. Presently such obstructions are circumvented surgically by grafting a bypass or they are treated by angioplasty with a catheter equipped with a balloon which is inserted, over a guide wire, into the obstruction through the arterial system and then inflated to expand the obstruction's lumen. Problems with this treatment are that it injures the arterial wall and may burst it and in certain cases it is ineffective. Further, it creates a rough lumen and does not remove the obstruction material out of the arterial system, therefore in a case of a heart attack, immediate angioplasty carries the risk of dislodging the blood clot and allowing it to move down stream creating further damage.

The objective of the present invention is to provide a catheter rotatable over a flexible guide-wire, equipped with a tubular-blade attached to its front end, that would cut and extract the obstruction material, including blood clots if present, create a smooth lumen and would not crack or injure the arterial wall. The mechanical atherectomy system should be produceable in diameters down to around 1 mm (millimeter) and a length of up to a meter to be able to reach and enter small and remote arteries. Preferably, the operation of the mechanical atherectomy system would resemble the operation of present catheters, as much as possible, so present skills of the medical staff can be utilized. This and other objectives of the invention will become apparent from the following discussion and the accompanying drawings.

BRIEF DESCRIPTION OF THE FIGURES

FIG. 1 shows a general cross sectional view of a mechanical atherectomy system inserted into an obstructed artery. The central portion of the mechanical atherectomy system is removed and is represented by a phantom line due to space limitations on the drawing sheet.

FIG. 2 shows a front end area of the mechanical atherectomy system with a tubular-blade retracted in a sleeve.

FIG. 3 shows a front, partially cross sectional view, of the mechanical atherectomy system along a line 3—3 marked on FIG. 2.

FIG. 4 shows a cross sectional view of the mechanical atherectomy system along a line 4—4 marked on FIG. 2.

FIG. 5 shows a cross sectional view of the mechanical atherectomy system along a line 5—5 marked on FIG. 2.

FIG. 6 shows a cross sectional view of an enlarged portion of a reinforced flexible rotary catheter.

FIG. 7 shows an optional flexible rotary catheter with an integral blade and an optional flexible guide-wire.

FIG. 8 shows an optional tubular-blade with a protruding rounded tooth.

FIG. 9 shows a side cross-sectional view of an optional flexible rotary catheter and an optional tubular-blade having triangular teeth and means for heating the blade. The central portion of the flexible rotary catheter is removed due to space limitations on the drawing sheet.

FIG. 10 shows a front view of the tubular-blade of FIG. 9.

FIG. 11 shows a mechanical atherectomy system in an artery with an optional sleeve having a tongue. The central portion of the mechanical atherectomy system has been removed due to space limitations on the drawing sheet.

FIG. 12 shows the front portion of the mechanical atherectomy system of FIG. 11 in an artery with an eccentric obstruction.

FIG. 13 shows a cross-sectional view of the tongue in the artery with the eccentric obstruction, as viewed along line 13—13 marked on FIG. 12.

FIG. 14 shows a mechanical atherectomy system with an optional remotely bendable sleeve.

FIG. 15 shows a cross sectional view of the bent area of the flexible tube of FIG. 14 having reinforcement and a restraint means built into its wall for improving rotation and torque transmission.

FIG. 16 shows a mechanical atherectomy system with an optional stepped diameter flexible rotary catheter. The central portion of the mechanical atherectomy system has been removed due to space limitations on the drawing sheet.

DETAILED DESCRIPTION OF THE DRAWINGS

FIG. 1 generally shows a mechanical atherectomy system 10 insertable into a patient's artery 11 over a flexible guide-wire 12 (similar parts are identified with same numbers throughout the FIGS.) for remotely cutting and removing an obstruction therein. The mechanical atherectomy system 10 comprises:

A flexible rotary catheter 14 having a front end 15 and a rear end 16, the flexible tube being rotatable around and slidable along the flexible guide-wire 12.

A tubular-blade 17 mounted to the front end 15. The term tubular-blade, as used herein, means a blade which cuts a narrow circular pass on a periphery of the obstruction 13 and separates the center core of the obstruction. The tubular-blade 17 has a through-hole 17′, which forms a continuous passage with the longitudinal hole defined by the flexible rotary catheter 14. The cut obstruction material is ingested through the through-hole and passed into the flexible tube 14. The tubular-blade 17 is sharpened along a circular line 19 as shown in FIG. 3. A tubular-blade is efficient and requires less energy input, in comparison to blades which pulverize the obstruction material. To illustrate this point, when the tubular-blade 17 extracts an obstruction with an outside diameter of 3 mm, an inside diameter (lumen) of 1 mm and a length of 10 mm the area that the tubular-blade 17 has to cut through is approximately 100 square mm. If a conventional blade, for example as shown in U.S. Pat. No. 4,445,509 by Auth, is used to break the same obstruction to shavings measuring 0.1 mm by 0.1 mm by 0.1 mm the area that the conventional blade would have had to cut through is approximately 3800 square mm, and this much larger area requires a much larger energy input to the blade increasing the probability of traumatizing the artery.

FIG. 7 shows an optional tubular-blade 118 formed integral at the end of the flexible rotary catheter 114. The edge 114' can be chemically or otherwise hardened, and teeth can be formed on it to enhance its cutting ability. This design has a lower probability of injuring the arterial wall, and may deal effectively with blood clots and soft obstruction materials. Since the blade is less aggressive by choice of material, its edge 114' can be formed on the outer diameter of the blade, whereas in the case of the tubular-blade 17 of FIG. 1 which is made of steel, the edge is preferably formed on a slightly smaller diameter to keep it away from the arterial wall, even when the side of the tubular blade bears against the arterial wall. To further enhance cutting ability of the blade 118 abrasive particles can be embedded in it, preferably on the side of inclined surface 113 which does not contact the arterial wall.

FIG. 8 shows an optional tubular-blade 18 having a protruding rounded tooth 18' which, like the tubular-blade 17, cuts the obstruction along a narrow peripheral path. Only a face 98 of tooth 18' needs to be sharpened, which reduces the probability of injuring the arterial wall when advancing the tubular-blade 18 toward the obstruction.

FIGS. 9 shows an optional flexible rotary-catheter 40 and an optional tubular-blade 41 having protruding triangular teeth 42 which also cut the obstruction along a narrow peripheral path. As in the embodiment of FIG. 8, only the tooth's face 43 (tooth's face designates the side of the tooth that moves into the obstruction material while the blade rotates forward, in the direction of arrow 38' of FIG. 10) needs to be sharpened while the back of tooth 44 is kept dull. This feature allows to rotate the blade backwards while it is being inserted towards the obstruction, past sharp curves in the arterial system, in order to assure that the sharp faces of the teeth 43 will be continuously retracting, and thereby their cutting action will be nulled. The face of the tooth 43 is shown inclined inward and backward by angles 45 and 46, respectively. The angle 45 urges the cut obstruction material to slide into the through-hole 48 rather than pile up on the face 43 while the angle 46 helps fiberous material to slide off, over the face 43 rather than get caught on it and interfere with the tubular-blade's operation.

Referring back to FIG. 1, a motor 20 has a shaft 21 with a drilled through passage 22 and a tapered end 23 which is connected to coupling means in the form of a matching tapered seat 24 integral with the rear end 16. The motor 20 rotates the flexible rotary catheter 14 and the tubular-blade 17 in a direction shown by arrow 38 (clockwise, when viewing from the rear end of the flexible rotary-catheter). The flexible rotary-catheter 14 is preferably made of plastic material and an optional reinforcing means in the form of wire shaped as a spiral spring 25. The spring 25 increases the torque carrying capacity and resists the collapse of flexible rotary-catheter 14, especially when the flexible rotary-catheter 14 is bent because of curves in the arterial system. The spring 25 is wound in a direction that causes its diameter to contract due to torque transmitted through it.

A portion of the length of the flexible guide-wire 12 which is located near the front end 15 is shaped as an auger 26 which is formed by a spaced spiral-wire 27 attached to the core-wire 28. The spiral-wire 27 extends beyond the core-wire 28 to form a soft spring 29 which can be gently pushed through the artery 11 and the obstruction's lumen. During operation the auger 26 accurately guides the flexible rotary-catheter 14 on the flexible guide-wire 12 and mechanically conveys obstruction material into the flexible rotary-catheter 14. A portion of the flexible guide-wire 12 that is further away from the front end 15 can be made of the core-wire 28 alone to minimize friction between the flexible guide-wire 12 and the flexible rotary-catheter 14. An optional flexible guide-wire 12' shown in FIG. 7 has a bare core-wire 28' extending forward of the auger for entering an obstruction with an extremely narrow lumen. An optional small ridge 14' is formed integral with the flexible rotary-catheter 14 on its inner wall urges the rotation of the obstruction material inside the flexible rotary-catheter 14. The ridge 14' starts at the vicinity of the first end 15 and longitudinally extends along the auger 26.

Optionally, as shown in FIG. 1, a thin wall tube containing a bundle of optical fibers 80 can serve as the core-wire 28. The bundle 80 optically connects a lens 81 affixed at the front end of the spring 29 to a light source and viewing unit 82 at the rear end of the flexible guide-wire. Some of the optical fibers can be used to transmit light from the unit 82 onto a target area in front of the lens 81 and other optical fibers to carry back the image to the unit 82 for viewing.

Preferably, the flexible rotary-catheter 14 is rotatably disposed in a sleeve 30 having a front opening 31 and a rear opening 32. When the mechanical atherectomy system 10 is inserted into the artery 11, the flexible rotary-catheter 14 and tubular-blade 17 are kept retracted in the sleeve 30 as shown in FIG. 2, to prevent injury to the artery 11. The rear end 16 extends outwardly from the rear opening 32. Upon reaching the obstruction's site, the rear opening 32, which is formed integral with a rotary fluid joint 33, is held in place and the flexible rotary-catheter 14 is pushed to slide in the sleeve 30 and push the tubular-blade 17 through the front opening 31 of the sleeve 30, as shown in FIG. 1. The front opening 31 is smaller in diameter than the tubular-blade 17, but it contains two slits 34 which make it flexible enough to allow the tubular-blade 17 to pass through. The sleeve can be inserted into the artery through an introducer, or it can serve as the introducer. Optionally, the sleeve can be pre-bent to serve as a guiding catheter and lead the flexible rotary-catheter and tubular-blade to a certain point in the arterial system.

As shown in FIGS. 11 and 12 a modified sleeve 60 has a tongue 60' for protecting the arterial wall 62 while the blade 17 cuts an eccentric obstruction 61. The tongue 60' may be especially useful when the obstruction material is hard and/or the arterial wall is weak.

FIG. 14 shows a remotely bendable-sleeve 70 for directing a flexible rotary-catheter 141 and tubular-blade inside the arterial system toward an obstruction 71 located in an entrance of a branch artery 75, while avoiding damage to arteries 75 and 76. The selectively bendable sleeve 70 comprises a handle 72 which through a cable 73 is connected to a ring 74 which is aifixed in the front end of the bendable sleeve 70. The cable 73 passes and is slidable in a wall of the bendable-sleeve 70, and when the handle 72 is pulled, it bends the bendable-sleeve 70 to a position as shown in FIG. 14, otherwise, when no force is exerted on the handle 72, the bendable-sleeve 70 is straight. The flexible rotary-catheter 141 has a reinforcing torque carrying spiral member in its wall in the form of a spring 77 wound in a direction that if its front end is stopped while the rear end of the flexible rotary-catheter 141 is rotated, in the direction of arrow 38 of FIG. 1, the spring would become unwound and diametrically expand. To prevent such expansion a hoop member in the form of narrowly spaced thin rope windings 78 around the spring 77 acts to restrain its diametrical expansion under torque. As can be seen, the cross section of the spring's winding is semi-circular, offering the rope windings 78 a flattened area to bear against. This construction allows the flexible rotary-catheter 141 to be flexible and bend in order to assume the sharp curves found in the arterial system while transferring torque to the tubular blade.

A blade heating system shown in FIG. 9 comprises a heating element 50 which is connected through wires 51 and 52, laid in the wall of the flexible rotary-catheter 40, to conductive rings 53 and 54, respectively. The rings are conductively connected to a battery 55 through sliding contacts 56 and 57. The heating element 50 is located close to the cutting edge of the blade so that when a switch 58 is closed electrical current passes through the heating element 50 and heats the cutting edge while the area of the blade which attaches to the flexible rotary-catheter 40, which usually comprises plastic materials, remains relatively cold. The heating element 50 is made of resistive wire whose electrical resistance increases at higher temperature, decreasing the current through it and thereby automatically regulating the temperature to avoid overheating the blade. The heat assists the blade in penetrating the obstruction and can be applied selectively as needed by switch 58.

Referring back to FIG. 1, suction means 35 are connected to the rear end 16, through the passage 22 and a rotary fluid joint 39, to assist in pulling obstruction materials including blood clots into through the flexible rotary-catheter 14, however, care should be given to the level of negative pressure created in the artery 11 not to collapse it. The suction is especially effective in combination with the auger's action.

Means 36 for introducing fluid to the vicinity of the tubular-blade 17 are connected to the rear opening 32 through the rotary fluid joint 33 which has an integral seal 37. The rotary fluid joint 33 directs the fluid into the sleeve 30 around the flexible rotary-catheter 14 and does not interfere with the rotation of the flexible rotary-catheter 14 in the sleeve 30.

It can be appreciated that the torque generated by the motor 20 is partially dissipated by frictional losses along the rotating flexible rotary-catheter, therefore, the flexible rotary-catheter can be manufactured with a variable cross section, i.e., a larger diameter and/or wall thickness at the vicinity of the rear end than in the vicinity of the front end. The cross sectional change can be gradual or in steps. This gives the flexible rotary catheter the required increased torque carrying capacity in the vicinity of its rear end. This refinement of design is useful, for example, when treating small arteries of the heart or brain while entering into the arterial system at the groin area. This requires a long flexible rotary catheter having a front end portion as small as 1 mm. FIG. 16 shows a stepped diameter flexible rotary catheter 90 having a blade 91. Since the arteries that are used as a corridor for reaching the heart or brain are of a larger diameter there is usually no problem in accommodating a rear larger diameter portion of the flexible rotary catheter 92 until the last several inches where the diameter of a front portion 93 of the flexible rotary-catheter is stepped down to enter the smaller arteries. The flexible rotary catheter of FIG. 16 can be accommodated in a matching, stepped sleeve (not shown).

It can be noted in general, that the mechanical atherectomy system can be manufactured in different diameters and lengths depending on the size and site of artery the it is intended for. By making the flexible guide-wire also function as an auger, and by driving the tubular blade through a flexible rotary-catheter which also serves as a catheter, compactness is achieved allowing the mechanical atherectomy system to be made to enter obstructed arteries which have a nominal lumen of around 1 mm.

OPERATION

A process for removing an obstruction from an artery comprises the following steps:

Inserting into the artery the flexible guide-wire and the flexible rotary catheter with the tubular-blade, preferably disposed in the sleeve, to the vicinity of the obstruction in the artery.

Placing the front portion of the flexible guide-wire in the obstructed area as shown in FIG. 1. This is a common procedure for inserting standard catheters and should not pose special problems or risks. The flexible guide-wire can be manually manipulated and in a case of a tight obstruction, rotated backwards in an opposite direction of arrow 38, so that the auger section screws itself or otherwise works its way into the obstruction. The soft spring minimizes the danger of perforating the arterial wall. The soft spring can be pre-shaped in cases where the flexible guide-wire has to be inserted into an arterial branch, similar to the present practice of shaping the tips of standard guide-wires. An optional visualizing system can further assist in inserting the flexible guide-wire through the lumen.

Once the flexible guide-wire is in place, the flexible rotary catheter and the tubular-blade are advanced to the obstruction site, and continue to be advanced into the obstruction while being rotated over the flexible guide-wire. The flexible guide-wire and the sleeve are prevented from being rotationaly dragged by the flexible rotary catheter. As the tubular-blade cuts the obstruction and ingests its material, the material, due to friction and adherence to the through hole and the wall of the flexible rotary catheter, starts rotating with them around the auger which pulls the material into the flexible rotary catheter. The small ridge 14' assists the friction in rotating the material around the auger. As the auger pulls the obstruction material into the flexible rotary catheter, it makes room for additional material to be ingested. Suction in the flexible rotary catheter assists with the mechanical conveying action of the auger while the auger's action assists the suction to reach the through hole without becoming blocked by the ingested obstruction material.

Finally, the mechanical atherectomy system containing the obstruction material is withdrawn out of the artery.

During the cutting the front end of the flexible rotary catheter and tubular-blade are accurately guided by the flexible guide-wire since the outside diameter of the auger is, preferably, close to the inside diameter of the flexible tube. The accurate guidance of the tubular-blade reduces the probability of cutting the arterial wall, especially when cutting along a curved artery as illustrated in FIG. 1. It can be seen that a solid wire having the same diameter as the auger would prevent, rather than assist, the obstruction material from entering the flexible rotary catheter. A thin flexible guide-wire, such as core wire by itself, would not provide accurate guidance nor would it provide positive conveying of obstruction materials into the flexible rotary catheter.

Fluid can be delivered to the obstruction site through the sleeve, around the flexible rotary-catheter. Such fluid can lubricate the rotation of the flexible rotary-catheter in the sleeve, irrigate the cutting site and act as a flushing medium of obstruction particles into the flexible rotary-catheter, especially in conjunction with suction applied to the flexible rotary-catheter. The fluid may be radio-opaque to assist x-raying the process. Alternatively, prior to cutting, fluid can also be delivered through the flexible rotary-catheter.

Diameter and length of the rotary-catheter components may vary in relation to the size and location of the artery that they are intended for. The sequence of insertion of the components into the artery may vary depending on the nature and the location of the obstruction. A standard guiding catheter, which is either straight or pre-bent, may be inserted first to assist in properly placing the flexible-guide-wire in the obstruction site, then the standard guiding catheter is withdrawn while the flexible guide-wire remains in place and then the rest of the components of the mechanical atherectomy system can be slid over the flexible guide-wire to the obstruction site, or if the guiding catheter is made to serve as a sleeve it does not have to be withdrawn, instead the flexible rotary-catheter and with the tubular-blade is slid over the flexible guide-wire and through the guiding catheter to cut the obstruction. When dealing with a total obstruction through which a flexible guide-wire can not be passed the flexible rotary-catheter can be used without the flexible guide-wire. This increases the risk of perforating the arterial wall, and a lower effectiveness in capturing and removing the obstruction material.

When an arterial obstruction is further blocked by a fresh blood clot, as is often the case in a heart attack, the flexible guide-wire can usually be inserted through the clot and the mechanical atherectomy system can be used to first clear the clot, preferably employing suction, and continue and drill through the older obstruction. Therefore, the mechanical atherectomy system can be effective in immediate treatment of a heart attack, where the treatment will relieve the life threatening stage and continue to provide a long term correction of the condition that induced the attack.

Differing strategies can be employed when dealing with the process of opening an arterial obstruction. A tubular-blade having an area equal to the artery's internal area can be chosen, however this poses a danger of injuring the internal arterial lining, or of leaving a thin layer of obstruction material left hanging on the arterial wall. Such a thin layer which has no structural integrity of its own may separate from the arterial wall and act as a flap of a one way valve which may block the artery and cause a blood clot. Therefore, an alternative strategy is to choose a tubular-blade with an area of less than three quarters of the area of the arterial lumen. Drilling the obstruction with such a tubular-blade usually relieves the patient's symptoms and it leaves sufficient material for the obstruction to remain structurally stable, reducing the likelihood of creating a flap. FIG. 1 illustrates this approach where the core portion of the obstruction that is to be removed is indicated with numeral 13' and is separated from the portion that is to remain the artery 13 by a phantom line. By using an undersized tubular-blade the likelihood of injuring the arterial wall is also reduced, even when dealing with an eccentric obstruction. After the obstruction's core 13' is removed it is also possible to further increase the lumen by balloon dilatation, however this will introduce some of the undesirable side effects that are associated with balloon angioplasty, and the choice of strategy will depend on the individual case's specific characteristics.

While the present invention has been illustrated by a limited number of embodiments, it should be understood that various modifications and substitutions may be made without departing from the spirit of the invention or the scope of the claims.

I claim:

1. A mechanical atherectomy system insertable into a patient's artery for remotely cutting and removing an obstruction therein, comprising in combination:
   a flexible guide-wire insertable into a patient's artery,
   a flexible rotary-catheter with front and rear ends, said flexible rotary-catheter being rotatably disposed and slidable over said flexible guide-wire,
   a tubular-blade mounted to said front end, said tubular-blade having a cutting edge at least part of which is sharpened, to cut a circular pass in an obstruction placed in front of it, said tubular-blade having a through-hole which defines together with said flexible rotary-catheter a continuous passage around said guide-wire for accepting obstruction material through said through-hole into said flexible rotary-catheter,
   coupling means affixed to said rear end for coupling said flexible rotary-catheter to rotating means.

2. A mechanical atherectomy system as in claim 1, wherein said tubular-blade has at least one tooth.

3. A mechanical atherectomy system as in claim 2, wherein said tooth has a sharp face and a dull back.

4. A mechanical atherectomy system as in claim 2, a face of said tooth being inclined inward, urging cut obstruction material into said through-hole.

5. A mechanical atherectomy system as in claim 2, wherein said face of said tooth is inclined backwards to allow obstruction material to slide off said tooth.

6. A mechanical atherectomy system as in claim 1, wherein tubular-blade is formed an integral part of said flexible rotary-catheter.

7. A mechanical atherectomy system as in claim 6, said tubular-blade having at least one tooth.

8. A mechanical atherectomy system as in claim 6, said tubular-blade having hard particles embedded in it.

9. A mechanical atherectomy system as in claim 1, having means for heating said tubular-blade.

10. A mechanical atherectomy system as in claim 1, wherein said flexible rotary-cathether has a larger diameter in the vicinity of said rear end than in the vicinity of said front end.

11. A mechanical atherectomy system as in claim 1, wherein said flexible rotary-catheter has a higher torque carrying capacity in the vicinity of said rear end than in the vicinity of said front end.

12. A mechanical atherectomy system as in claim 1, wherein suction means are connected to said flexible rotary-catheter.

13. A mechanical atherectomy system as in claim 1, having a sleeve with a front opening and a rear opening, said flexible rotary-catheter being rotatably disposed in said sleeve.

14. A mechanical atherectomy system as in claim 13, said sleeve having a tongue.

15. A mechanical atherectomy system as in claim 13, said sleeve being remotely bendable.

16. A mechanical atherectomy system as in claim 13, wherein said sleeve being pre-bent to serve as a guiding catheter.

17. A mechanical atherectomy system as in claim 13, wherein said front opening is smaller in diameter than said tubular-blade to ease penetration of said mechanical atherectomy system into said artery.

18. A mechanical atherectomy system as in claim 13, wherein means for introducing fluids into the artery are connected to said sleeve.

19. A mechanical atherectomy system as in claim 1, wherein said flexible rotary-catheter has a torque carrying spiral member in its wall.

20. A mechanical atherectomy system as in claim 19, having a hoop member around said spiral member for restraining the diametrical expansion of said spiral member.

21. A process for mechanically removing an obstruction from an artery, comprising the following steps:
   inserting into an artery, into an obstruction, a flexible guide-wire and a flexible rotary-catheter having a tubular-blade attached to its front end,
   rotating said flexible rotary-catheter and tubular-blade around said flexible guide-wire while advancing said flexible rotary-catheter and said tubular blade into said obstruction, thereby peripherally cutting said obstruction and ingesting its material into said flexible rotary-catheter,
   removing said flexible guide-wire and flexible rotary-catheter containing said obstruction material out of said artery.

22. A process as in claim 21, wherein suction is maintained in said flexible rotary-catheter.

23. A process as in claim 21, wherein a sleeve is disposed in the artery and at least a portion of said flexible rotary-catheter is rotated in said sleeve.

24. A process as in claim 23, wherein fluid is delivered through said sleeve.

25. A process for removing an obstruction from an artery, comprising the following steps:
   inserting into an artery a sleeve toward the obstruction site,
   inserting through said sleeve a flexible guide-wire into the obstruction,
   inserting over said flexible guide-wire a flexible rotary-catheter with a tubular-blade attached to its front end, to the obstruction site,
   rotating said flexible rotary-catheter and tubular-blade around said flexible guide-wire while advancing said flexible rotary-catheter and tubular-blade into the obstruction, thereby peripherally cutting said obstruction and ingesting its material into said flexible rotary-catheter,
   removing said flexible guide-wire and flexible rotary-catheter containing said obstruction material out of said artery.

26. A process as in claim 25, wherein suction is maintained in said flexible rotary-catheter.

27. A process as in claim 25, wherein fluid is delivered into the artery through said sleeve.

* * * * *